(12) United States Patent
Huang et al.

(10) Patent No.: US 9,119,894 B2
(45) Date of Patent: Sep. 1, 2015

(54) METHOD FOR MODIFYING NON-WOVEN CHITOSAN FABRIC

(71) Applicant: QINGDAO JIFA NEW MATERIAL CO., LTD., Qingdao (CN)

(72) Inventors: Yuhua Huang, Qingdao (CN); Weidong Yang, Qingdao (CN); Hongjun Yi, Qingdao (CN)

(73) Assignee: QINGDAO JIFA NEW MATERIAL CO., LTD., Qingdao (CN)

( * ) Notice: Subject to any disclaimer, the term of this patent is extended or adjusted under 35 U.S.C. 154(b) by 33 days.

(21) Appl. No.: 13/912,174

(22) Filed: Jun. 6, 2013

(65) Prior Publication Data

US 2013/0273235 A1    Oct. 17, 2013

Related U.S. Application Data

(63) Continuation-in-part of application No. PCT/CN2010/080431, filed on Dec. 29, 2010.

(30) Foreign Application Priority Data

Dec. 8, 2010 (CN) .......................... 2010 1 0577687

(51) Int. Cl.
- *A61L 33/00* (2006.01)
- *A61L 15/42* (2006.01)
- *A61L 15/28* (2006.01)
- *D06M 13/192* (2006.01)
- *A61L 15/62* (2006.01)

(52) U.S. Cl.
CPC .................. *A61L 15/42* (2013.01); *A61L 15/28* (2013.01); *A61L 15/62* (2013.01); *D06M 13/192* (2013.01)

(58) Field of Classification Search
CPC ....................................................... A61L 33/00
USPC ...................................... 427/2.31, 2.24, 2.25
See application file for complete search history.

(56) References Cited

FOREIGN PATENT DOCUMENTS

CN      101624778 B  *  5/2012  .............. A61L 33/00

* cited by examiner

*Primary Examiner* — Dah-Wei D Yuan
*Assistant Examiner* — Andrew Bowman
(74) *Attorney, Agent, or Firm* — Matthias Scholl P.C.; Matthias Scholl

(57) ABSTRACT

A method for modifying a non-woven fabric of chitosan fiber. The method includes: adding succinic anhydride to an industrial alcohol, ethanol, or acetone; controlling the mass ratio of succinic anhydride to the non-woven fabric at between 0.8 and 3.5; and stirring the resulting mixture until the succinic anhydride has dissolved to yield a succinic anhydride mixed solution; placing the succinic anhydride mixed solution in a constant temperature shaking bath; heating the succinic anhydride mixed solution; adding an HCl solution to the succinic anhydride mixed solution, and stirring evenly to yield a HCl mixed solution; immersing the non-woven fabric in the HCl mixed solution; dehydrating; immersing the non-woven fabric in ethanol or acetone; immersing the non-woven fabric in anhydrous ethanol or pure acetone; dehydrating; and air drying the non-woven fabric.

3 Claims, No Drawings

METHOD FOR MODIFYING NON-WOVEN CHITOSAN FABRIC

CROSS-REFERENCE TO RELATED APPLICATIONS

This application is a continuation-in-part of International Patent Application No. PCT/CN2010/080431 with an international filing date of Dec. 29, 2010, designating the United States, and further claims priority benefits to Chinese Patent Application No. 201010577687.7 filed Dec. 8, 2010. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 14781 Memorial Drive, Suite 1319, Houston, Tex. 77079.

BACKGROUND OF THE INVENTION

1. Field of the Invention

The invention relates to a manufacturing process of a water soluble non-woven fabric, and more particularly to a method for modifying a non-woven fabric made of chitosan fiber.

2. Description of the Related Art

Medical dressing made of non-woven fabric has been more and more widely used in the field of producing wound healing material. Chitosan is endowed with many natural capabilities. It is anti-bacterial, anti-inflammatory, and hemostatic. It promotes wound healing and reduction of wound scarring. And, it has good biocompatibility.

A typical method for producing chitosan fiber non-woven fabric includes: wet spinning the chitosan into fibers, and further spinning the chitosan fibers into a non-woven fabric that is applicable to the wound healing materials. However, the chitosan fiber non-woven fabric prepared by using the above method is capable of adsorbing only a small amount of wound effluent when it is applied over the wound, and the chitosan fiber non-woven fabric cannot retain moisture around the wound, so that the chitosan fiber non-woven fabric is prone to stick to the skin after the wound has healed, thereby resulting in inconvenience in practice.

To solve the above-mentioned problems, desired is a non-woven fabric made of chitosan fibers that is able to adsorb a larger amount of the wound effluent, and that has a certain viscosity after being dissolved so that it will stick to the wound during healing and will fall off after the wound has healed.

SUMMARY OF THE INVENTION

In view of the above-described problems, it is one objective of the invention to provide a method for modifying a non-woven fabric made of chitosan fiber. The non-woven fabric made of chitosan fiber modified by the method is water soluble and instantly dissolved in the presence of water or an aqueous solution to form a viscid solution, that is, the non-woven fabric is able to adsorb the wound effluent as well as stick to the wound, and is particularly applicable to a stanching and healing dressing for unfixed cavity wounds, such as nasal cavity wounds and cervical wounds after surgery.

To achieve the above objective, in accordance with one embodiment of the invention, there is provided a method for modifying a non-woven fabric made of chitosan fiber, the method comprising the following steps:

1) adding succinic anhydride to an industrial alcohol having a concentration of 70% or more, ethanol having a concentration of 70% or more, or acetone having a concentration of 70% or more; controlling the mass ratio of the succinic anhydride to the non-woven fabric made of chitosan fiber between 0.8 and 3.5; and stirring a resulting mixture until the succinic anhydride has dissolved to yield a succinic anhydride mixed solution;

2) placing the succinic anhydride mixed solution in a constant temperature shaking bath; heating the succinic anhydride mixed solution to a temperature between 30 and 70° C. and shaking at that temperature; adding a HCl solution to the succinic anhydride mixed solution, and stirring evenly to yield a HCl mixed solution; and controlling the mass ratio of hydrochloric acid to the non-woven fabric at between 0.12 and 0.4;

3) shaking the HCl mixed solution at a constant temperature of between 30 and 70° C.; immersing the non-woven fabric in the HCl mixed solution for between 2 and 8 h;

4) taking the non-woven fabric out of the HCl mixed solution; dehydrating; immersing the non-woven fabric in ethanol having a concentration of 90% or more or acetone having a concentration of 90% or more; allowing the immersed fabric to soak for more than 40 min; and taking the non-woven fabric out for dehydration; and 5) immersing the non-woven fabric in anhydrous ethanol or pure acetone for between 3 and 5 times to displace water in the non-woven fabric; dehydrating; and air drying the non-woven fabric.

In a class of this embodiment, the non-woven fabric is a stitch bonded non-woven fabric or a spunlace non-woven fabric prepared from a purified chitosan fiber according to a conventional method.

In a class of this embodiment, the volume of the industrial alcohol having the concentration of 70% or more, the ethanol having the concentration of 70% or more, or the acetone having the concentration of 70% or more is sufficient to fully immerse the non-woven fabric.

Advantages of the invention are summarized as follows. The non-woven fabric made of chitosan fiber modified by using the above method is water soluble and instantly dissolved to form a viscid solution, thereby enabling the non-woven fabric made of chitosan fiber to adsorb the wound effluent and stick to the wound. The modified non-woven fabric made of chitosan fiber is particularly applicable to a stanching and healing dressing for unfixed cavity wounds, such as nasal cavity wounds and cervical wounds after surgery.

DETAILED DESCRIPTION OF THE EMBODIMENTS

A method for modifying a non-woven fabric made of chitosan fiber, comprises the following steps:

Step 1): add succinic anhydride to an industrial alcohol having a concentration of 70% or more, ethanol having a concentration of 70% or more, or acetone having a concentration of 70% or more; preferable concentrations are: 70%, 75%, 80%, 85%, 90%, 95%, and 100%. Control the mass ratio of the succinic anhydride to the non-woven fabric at between 0.8 and 3.5; preferable mass ratios are 0.8, 0.9, 1, 1.5, 2, 2.5, 3, 3.5; and stir a resulting mixture until the succinic anhydride has dissolved to yield a succinic anhydride mixed solution.

The non-woven fabric made of chitosan fiber is a stitch bonded non-woven fabric or a spunlace non-woven fabric prepared from a purified chitosan fiber according to a conventional method.

The volume of the industrial alcohol having a concentration of 70% or more, ethanol having a concentration of 70% or more, or acetone having a concentration of 70% or more is sufficient for fully immersing the non-woven fabric.

Step 2): place the succinic anhydride mixed solution in a constant temperature shaking bath; heat the succinic anhydride mixed solution to a temperature of between 30 and 70° C.; preferable temperatures are: 30° C., 35° C., 40° C., 45° C., 50° C., 55° C., 60° C., 65° C., and 70° C. Shake the succinic anhydride mixed solution while maintaining the temperature constant. Add an HCl solution to the succinic anhydride mixed solution, stir evenly to yield an HCl mixed solution. Control the mass ratio of hydrochloric acid to the non-woven fabric at between 0.12 and 0.4; preferable mass ratios are: 0.12, 0.15, 0.2, 0.25, 0.3, 0.35, and 0.4.

Step 3): shake the HCl mixed solution at a constant temperature of between 30 and 70° C.; immerse the non-woven fabric in the HCl mixed solution for between 2 and 8 h; preferable durations are 2 h, 2.5 h, 3 h, 3.5 h, 4 h, 4.5 h, 5 h, 5.5 h, 6 h, 6.5 h, 7 h, 7.5 h, and 8 h.

Step 4): take the non-woven fabric out of the HCl mixed solution; dehydrate; immerse the non-woven fabric in ethanol having a concentration of 90% or more or acetone having a concentration of 90% or more; let the immersed fabric stand for more than 40 min; and then take the non-woven fabric out for dehydration.

Step 5): immerse the non-woven fabric in anhydrous ethanol or pure acetone for between 3 and 5 times to displace water in the non-woven fabric; dehydrate; and air dry.

The dehydration in the above technical scheme is conducted in a common dewatering centrifuge to remove water from the non-woven fabric, thereby realizing the purpose of the fast drying of the non-woven fabric. Specific time of the dehydration is determined by the quantity of the non-woven fabric.

The method for modifying the non-woven fabric made of chitosan fiber is characterized in that the modified non-woven fabric made of chitosan fiber is water soluble and instantly dissolved to form a viscid solution, so that it is capable of adsorbing wound effluent. The chitosan fiber has functions of fully contacting with the wound surface to fast adsorb the blood on the wound surface, anti-inflammation, and wound healing. Because after absorbing the wound effluent, the chitosan fiber is dissolved to yield a viscid solution, the non-woven fabric made of chitosan fiber is attached to the wound, so that it is applicable to the wound for which the dressing is difficult to fix, and more particularly applicable to a stanching and healing dressing for unfixed cavity wounds, such as nasal cavity wounds and cervical wounds after surgery.

After the wound is healed, the dressing on the surface will be condensed and will fall off, thereby largely reducing the suffering of patients.

For further illustrating the invention, experiments detailing the method for modifying the non-woven fabric made of chitosan fiber are described hereinbelow:

Example 1

Step 1): dissolve 10 g of succinic anhydride in 1000 mL of aqueous ethanol having a concentration of 80% v/v to yield a succinic anhydride mixed solution;

Step 2): place the succinic anhydride mixed solution in a constant temperature shaking bath; heat the succinic anhydride mixed solution to a temperature of 40° C.; shake the succinic anhydride mixed solution at that constant temperature; add 30 mL of a 2 mol/L HCl solution; and stir evenly to yield a HCl mixed solution;

Step 3): shake the HCl mixed solution at a constant temperature of 40° C.; immerse 10 g of a stitch bonded non-woven fabric made of chitosan fiber in the HCl mixed solution for 3 h;

Step 4): take the non-woven fabric out of the HCl mixed solution; dehydrate; immerse the non-woven fabric in ethanol having a concentration of 95% v/v; allow the immersed fabric to stand for more than 40 min; and then take the non-woven fabric out for dehydration; and Step 5): immerse the non-woven fabric in anhydrous ethanol for 3 times to displace water in the non-woven fabric; dehydrate; and air dry.

Example 2

Step 1): dissolve 50 g of succinic anhydride in 8 L of aqueous acetone having a concentration of 85% v/v to yield a succinic anhydride mixed solution;

Step 2): place the succinic anhydride mixed solution in a constant temperature shaking bath; heat the succinic anhydride mixed solution to a temperature of 65° C.; shake the succinic anhydride mixed solution at that constant temperature; add 75 mL of a 2 mol/L HCl solution; and stir evenly to yield a HCl mixed solution;

Step 3): shake the HCl mixed solution at a constant temperature of 65° C.; immerse 45 g of a stitch bonded non-woven fabric made of chitosan fiber in the HCl mixed solution for 4 h;

Step 4): take the non-woven fabric out of the HCl mixed solution; dehydrate; immerse the non-woven fabric in aqueous acetone having a concentration of 90% v/v; allow the immersed fabric to stand for more than 45 min; and take the non-woven fabric out for dehydration; and Step 5): immerse the non-woven fabric in pure acetone for 4 times to displace water in the non-woven fabric; dehydrate; and air dry.

Example 3

Step 1): dissolve 100 g of succinic anhydride in 20 L of an aqueous industrial alcohol having a concentration of 90% v/v to yield a succinic anhydride mixed solution;

Step 2): place the succinic anhydride mixed solution in a constant temperature shaking bath; heat the succinic anhydride mixed solution to a temperature of 60° C.; shake the succinic anhydride mixed solution at the constant temperature; add 120 mL of a 4 mol/L HCl solution; and stir evenly to yield a HCl mixed solution;

Step 3): shake the HCl mixed solution at the constant temperature of 60° C.; immerse 120 g of a stitch bonded non-woven fabric made of chitosan fiber in the HCl mixed solution for 5 h;

Step 4): take the non-woven fabric out of the HCl mixed solution; dehydrate; immerse the non-woven fabric in aqueous ethanol having a concentration of 95% v/v; let the immersed fabric stand for more than 60 min; and take the non-woven fabric out for dehydration; and Step 5): immerse the non-woven fabric in anhydrous ethanol for 4 times to displace water in the non-woven fabric; dehydrate; and air dry.

Example 4

Step 1): dissolve 20 g of succinic anhydride in 1 L of an aqueous industrial alcohol having a concentration of 85% v/v to yield a succinic anhydride mixed solution;

Step 2): place the succinic anhydride mixed solution in a constant temperature shaking bath; heat the succinic anhydride mixed solution to a temperature of 50° C.; shake the succinic anhydride mixed solution at that constant temperature; add 80 mL of a 2 mol/L HCl solution; and stir evenly to yield a HCl mixed solution;

Step 3): shake the HCl mixed solution at a constant temperature of 50° C.; immerse 15 g of a spunlace non-woven fabric made of chitosan fiber in the HCl mixed solution for 6 h;

Step 4): take the non-woven fabric out of the HCl mixed solution; dehydrate; immerse the non-woven fabric in aqueous ethanol having a concentration of 95% v/v; allow the immersed fabric to stand for more than 60 min; and take the non-woven fabric out for dehydration; and Step 5): immerse the non-woven fabric in anhydrous ethanol for 5 times to displace water in the non-woven fabric; dehydrate; and air dry.

Example 5

Step 1): dissolve 200 g of succinic anhydride in 10 L of an aqueous industrial alcohol having a concentration of 85% v/v to yield a succinic anhydride mixed solution;

Step 2): place the succinic anhydride mixed solution in a constant temperature shaking bath; heat the succinic anhydride mixed solution to a temperature of 45° C.; shake the succinic anhydride mixed solution at that constant temperature; add 160 mL of a 4 mol/L HCl solution; and stir evenly to yield a HCl mixed solution;

Step 3): shake the HCl mixed solution at a constant temperature of 45° C.; immerse 100 g of a spunlaced non-woven fabric made of chitosan fiber in the HCl mixed solution for 7.5 h;

Step 4): take the non-woven fabric out of the HCl mixed solution; dehydrate; immerse the non-woven fabric in aqueous ethanol having a concentration of 95% v/v; let the immersed fabric to stand for more than 50 min; and take the non-woven fabric out for dehydration; and Step 5): immerse the non-woven fabric in anhydrous ethanol for 5 times to displace water in the non-woven fabric; dehydrate; and air dry.

Example 6

Add 1.5000 g of the non-woven fabric modified by using each of examples 1-5 to 150 mL of distilled water; and stir until the non-woven fabric is completely dissolved to yield a mixture. Place the mixture in a 25° C. water bath until the temperature of the mixture increases to 25° C. Test the viscosity of the mixture by using a rotary viscometer. Viscosity data of the five groups of the mixture are 90 cps, 150 cps, 200 cps, 120 cps, and 180 cps, respectively (Cps represents a viscosity unit).

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method for modifying a non-woven fabric made of chitosan fiber, the method comprising:
   1) adding succinic anhydride to an aqueous industrial alcohol having a concentration of 70% or more v/v, aqueous ethanol having a concentration of 70% or more v/v, or aqueous acetone having a concentration of 70% or more v/v; controlling a mass ratio between the succinic anhydride and the non-woven fabric made of chitosan fiber at between 0.8 and 3.5; and stirring a resulting mixture until the succinic anhydride has dissolved to yield a succinic anhydride mixed solution;
   2) placing the succinic anhydride mixed solution in a constant temperature shaking bath; heating the succinic anhydride mixed solution to a temperature of between 30 and 70° C. and shaking at that temperature; adding an HCl solution to the succinic anhydride mixed solution, and stirring evenly to yield a HCl mixed solution; and controlling a mass ratio between hydrochloric acid and the non-woven fabric at between 0.12 and 0.4;
   3) shaking the HCl mixed solution at a constant temperature of between 30 and 70° C.; immersing the non-woven fabric in the HCl mixed solution for between 2 and 8 h;
   4) taking the non-woven fabric out of the HCl mixed solution; dehydrating; immersing the non-woven fabric in aqueous ethanol having a concentration of 90% or more v/v or aqueous acetone having a concentration of 90% or more v/v; allowing the non-woven fabric to stand for more than 40 min; and taking the non-woven fabric out for dehydration; and
   5) immersing the non-woven fabric in anhydrous ethanol or pure acetone for between 3 and 5 times to displace water in the non-woven fabric; dehydrating; and air drying the non-woven fabric.

2. The method of claim 1, wherein the non-woven fabric is a stitch-bonded non-woven fabric or a spunlace non-woven fabric prepared by using a purified chitosan fiber according to a conventional method.

3. The method of claim 1, wherein a volume of the aqueous industrial alcohol having the concentration of 70% or more v/v, the aqueous ethanol having the concentration of 70% or more v/v, or the aqueous acetone having the concentration of 70% or more v/v is sufficient to fully immerse the non-woven fabric.

* * * * *